(12) United States Patent
Tratrat et al.

(10) Patent No.: US 11,780,809 B1
(45) Date of Patent: Oct. 10, 2023

(54) CARBAZOLE COMPOUNDS AS ANTIBACTERIAL AGENTS

(71) Applicant: KING FAISAL UNIVERSITY, Al-Ahsa (SA)

(72) Inventors: Christophe Tratrat, Al-Ahsa (SA); Michelyne Haroun, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/119,742

(22) Filed: Mar. 9, 2023

(51) Int. Cl.
| | |
|---|---|
| *C07D 209/88* | (2006.01) |
| *C07D 403/10* | (2006.01) |
| *C07D 401/12* | (2006.01) |
| *A61P 31/06* | (2006.01) |
| *A61P 31/04* | (2006.01) |

(52) U.S. Cl.
CPC ............ *C07D 209/88* (2013.01); *A61P 31/04* (2018.01); *A61P 31/06* (2018.01); *C07D 401/12* (2013.01); *C07D 403/10* (2013.01)

(58) Field of Classification Search
CPC .. C07D 209/88; C07D 401/12; C07D 403/10; A61P 31/04; A61P 31/06
USPC ........................................................ 514/274
See application file for complete search history.

(56) References Cited

U.S. PATENT DOCUMENTS

| | | |
|---|---|---|
| 2001/0020846 A1 | 9/2001 | Miyata |
| 2022/0115594 A1 | 4/2022 | Pak et al. |
| 2022/0169609 A1 | 6/2022 | Pabbaraia et al. |
| 2022/0185775 A1 | 6/2022 | Zhao et al. |

FOREIGN PATENT DOCUMENTS

| | | |
|---|---|---|
| EP | 3962474 A1 | 3/2022 |
| WO | 2021/067657 A1 | 4/2021 |

OTHER PUBLICATIONS

Patpi et al., "Design, Synthesis, and Structure-Activity Correlations of Novel Dibenzo[b,d]furan, Dibenzo[b,d]thiophene, and N-Methylcarbazole Clubbed 1,2,3-Triazoles as Potent Inhibitors of *Mycobacterium tuberculosis*," Mar. 2012, Journal of Medicinal Chemistry, 55(8):3911-22.
3-phenyl-9H-carbazole, PubChem, 2007.

*Primary Examiner* — Kahsay Habte
(74) *Attorney, Agent, or Firm* — Nath, Goldberg & Meyer; Richard C. Litman

(57) ABSTRACT

The N-(6-substitutedcarbazol-2-yl) acetamide compounds are antibacterial agents. The emergence of drug-resistant bacteria calls for constant development of new antibacterial agents with the aim of generating medicaments that are potent against drug sensitive and resistant bacteria and are well tolerated. The present compounds are not only new, but have very valuable antimicrobial properties. These compounds showed a broad spectrum of activity against gram-positive and gram-negative bacteria, as well tuberculosis mycobacteria. They also showed potent activity against drug-resistant bacteria, such as MRSA and VRSA. The molecular target of these compounds was identified as DNA Gyrase B. Based on their pharmacological profiles, the present compounds may find important clinical applications for severe infectious diseases and tuberculosis.

17 Claims, No Drawings

CARBAZOLE COMPOUNDS AS ANTIBACTERIAL AGENTS

BACKGROUND

1. Field

The disclosure of the present patent application relates to carbazole compounds, and particularly to novel N-(6-substitutedcarbazol-2-yl) acetamide compounds as antibacterial agents.

2. Description of the Related Art

Infectious diseases caused by bacterial resistance to antibiotics constitute an increasing threat to humans on a global scale. An increasing number of infectious bacteria, including tuberculosis, pneumonia, salmonellosis and gonorrhea, are becoming progressively challenging to cure owing to the ineffectiveness of currently used clinical antibiotics and present a serious health threat worldwide in the medical community. The major concern of this global health threat is the ability of microorganisms to develop one or several mechanisms of resistance to antibiotics, rendering them inefficient for therapeutic treatment. The quest for discovering novel scaffolds with antimicrobial properties is particularly challenging in hospital and healthcare settings.

Similarly, the emergence of drug resistant bacteria calls for constant development of new antibacterial agents with the aim of generating medicaments that are potent against drug sensitive and resistant bacteria and are well tolerated.

Tuberculosis (TB) is one of the top 10 leading causes of mortality worldwide and is the leading cause of death from infectious disease among adults. It is a communicable disease caused by the bacterium *Mycobacterium tuberculosis* (MTB) that primarily affects the lungs, resulting in pulmonary TB. T13 can also infect other sites of the body, causing extrapulmonary TB.

To date, no major changes in the treatment of TB have been made, and the current standard treatment still involves a combination of four antibiotics (isoniazid, rifampin, pyrazinamide, and ethambutol) given for two months followed by isoniazid and rifampicin for an additional four months. This anti-TB regimen has been successful in the treatment of MTB H37Rv. However, the emergence of multidrug-resistant TB (MDR-TB) and extensively drug-resistant TB (XDR-TB), as well as HIV/TB co-infection cases, have made TB control more difficult. Moreover, treating resistant TB can take up to 24 months and might be associated with side effects and a low chance of cure. This, in turn, can lead to poor patient compliance, which can also contribute to the development of resistance.

Despite the efforts to discover new anti-TB compounds, current therapies are still facing the development of resistance and poor compliance due to long treatment duration. Therefore, it is evident that there is an urgent need for the development of new potential antimicrobial compounds generally, and anti-TB compounds specifically, that can act on new molecular targets to overcome drug-resistant MTB strains and to control the wide spread of TB.

Thus, new compounds as antibacterial agents solving the aforementioned problems are desired.

SUMMARY

The carbazole compounds as antibacterial agents, in one embodiment, relates to a compound having the formula I:

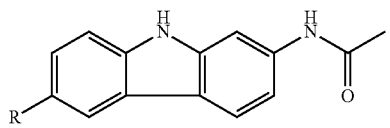

or a pharmaceutically acceptable salt, ester, stereoisomer, or solvate thereof, wherein: R is an aryl, heteroaryl, arylamine, or heteroarylamine, each of which may be optionally substituted with from one to three substituents.

In another embodiment, the present subject matter relates to a N-(6-substitutedcarbazol-2-yl)acetamide compound having the formula I:

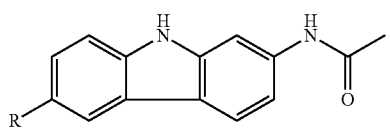

or a pharmaceutically acceptable salt, ester, stereoisomer, or solvate thereof, wherein R is a phenyl, a pyrimidine, a pyridine, an amino phenyl, an amino pyrimidine, or an amino pyridine, each of which phenyl, pyrimidine, and pyridine may be optionally substituted with from one to three substituents independently selected from the group consisting of hydrogen, a carboxylic acid group, a trifluoromethoxy group, a trifluoromethyl group, and a methoxy group.

In a further embodiment, the present subject matter relates to a compound selected from the group consisting of 3-(7-acetamido-9H-carbazol-3-yl)benzoic acid (1); N-(6-(3-(trifluoromethoxy)phenyl)-9H-carbazol-2-yl)acetamide (2); N-(6-(3-methoxyphenyl)-9H-carbazol-2-yl)acetamide (3); N-(6-(3-(trifluoromethyl)phenyl)-9H-carbazol-2-yl)acetamide (4); N-(6-(2-methoxypyrimidin-5-yl)-9H-carbazol-2-yl)acetamide (5); 3-((7-acetamido-9H-carbazol-3-yl)amino)benzoic acid (6); N-(6-((3-(trifluoromethoxy)phenyl)amino)-9H-carbazol-2-yl)acetamide (7); N-(6-((3-methoxyphenyl)amino)-9H-carbazol-2-yl)acetamide (8); N-(6-((3-(trifluoromethyl)phenyl)amino)-9H-carbazol-2-yl)acetamide (9); N-(6-(pyridin-3-ylamino)-9H-carbazol-2-yl)acetamide (10); and a pharmaceutically acceptable salt, ester, stereoisomer, or solvate thereof.

Further contemplated herein are pharmaceutical compositions containing these compounds, as well as methods of treating various bacterial infections by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In one embodiment, the present subject matter relates to a compound having the formula I:

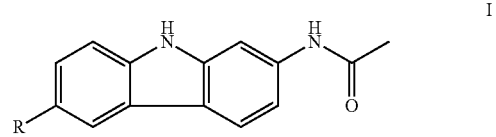

or a pharmaceutically acceptable salt, ester, stereoisomer, or solvate thereof, wherein:

R is an aryl, heteroaryl, arylamine, or heteroarylamine, each of which may be optionally substituted with from one to three substituents.

In one embodiment, the present subject matter relates to a compound of formula I, wherein each substituent of the from one to three substituents for R is independently selected from the group consisting of hydrogen, a carboxylic acid group, a trihalolkoxy group, a trihaloalkyl group, and an alkoxy group.

In another embodiment, the present subject matter relates to a compound of formula I, wherein each substituent of the from one to three substituents for R is independently selected from the group consisting of hydrogen, a carboxylic acid group, a trifluoromethoxy group, a trifluoromethyl group, and a methoxy group.

In a further embodiment, the present subject matter relates to a compound of formula I, wherein R is a phenyl, a pyrimidine, or a pyridine, each of which may be optionally substituted with from one to three substituents.

In yet another embodiment, the present subject matter relates to a compound of formula I, wherein R is an amino phenyl, an amino pyrimidine, or an amino pyridine, each of which phenyl, pyrimidine, and pyridine may be optionally substituted with from one to three substituents.

In certain embodiments, the present subject matter relates to a compound of formula I, wherein R is a phenyl, a pyrimidine, a pyridine, an amino phenyl, an amino pyrimidine, or an amino pyridine, each of which phenyl, pyrimidine, and pyridine may be optionally substituted with from one to three substituents independently selected from the group consisting of hydrogen, a carboxylic acid group, a trifluoromethoxy group, a trifluoromethyl group, and a methoxy group. In certain embodiments in this regard, R is selected from the group consisting of benzoic acid, 3-trifluoromethoxyphenyl, 3-methoxyphenyl, 3-trifluoromethylphenyl, 2-methoxypyrimidin-5-yl, amino benzoic acid, 3-trifluoromethoxyphenylamino, 3-methoxyphenylamino, 3-trifluoromethylphenyl, and pyridine-3-ylamino.

In another embodiment, the present subject matter relates to a compound of formula I, wherein the compound is selected from the group consisting of 3-(7-acetamido-9H-carbazol-3-yl)benzoic acid (1); N-(6-(3-(trifluoromethoxy)phenyl)-9H-carbazol-2-yl)acetamide (2); N-(6-(3-methoxyphenyl)-9H-carbazol-2-yl)acetamide (3); N-(6-(3-(trifluoromethyl)phenyl)-9H-carbazol-2-yl)acetamide (4): N-(6-(2-methoxypyrimidin-5-yl)-9H-carbazol-2-yl)acetamide (5); 3-((7-acetamido-9H-carbazol-3-yl)amino)benzoic acid (6); N-(6-((3-(trifluoromethoxy)phenyl)amino)-9H-carbazol-2-yl)acetamide (7); N-(6-((3-methoxyphenyl)amino)-9H-carbazol-2-yl)acetamide (8); N-(6-((3-(trifluoromethyl)phenyl)amino)-9H-carbazol-2-yl)acetamide (9); N-(6-(pyridin-3-ylamino)-9H-carbazol-2-yl)acetamide (10); and a pharmaceutically acceptable salt, ester, stereoisomer, or solvate thereof.

Said differently, the present subject matter can relate to compounds of formula I selected from the group consisting of:

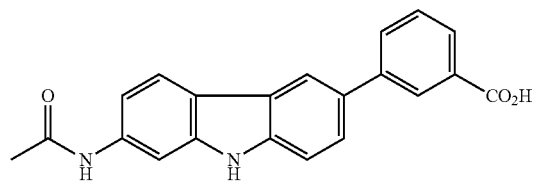

1

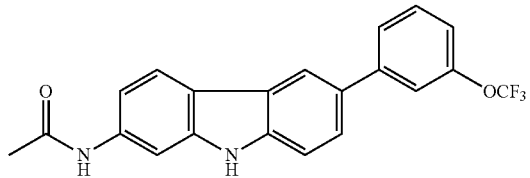

2

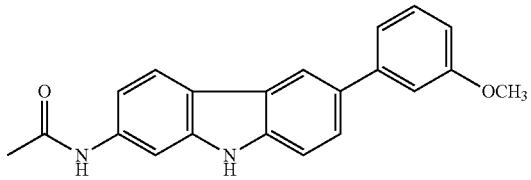

3

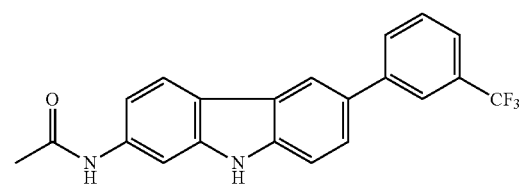

4

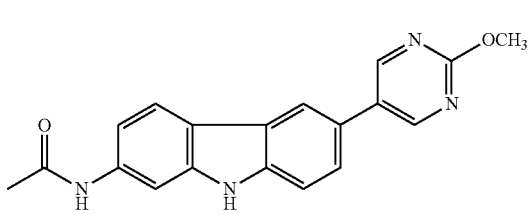

5

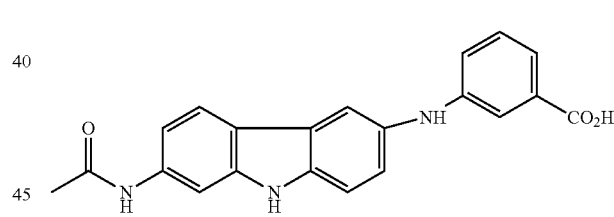

6

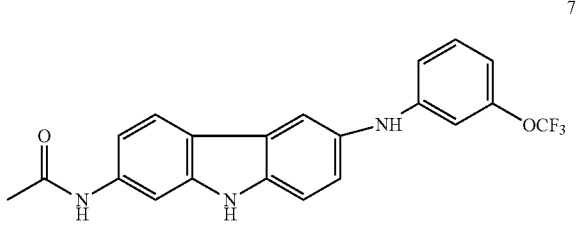

7

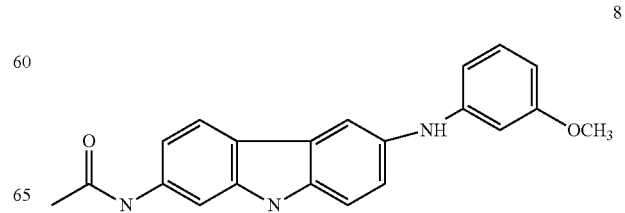

8

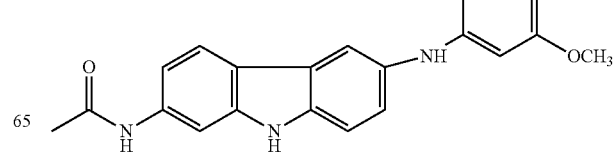

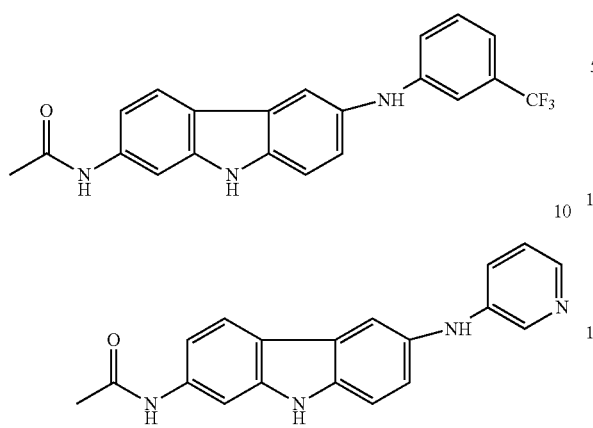

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or the salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following reaction scheme:

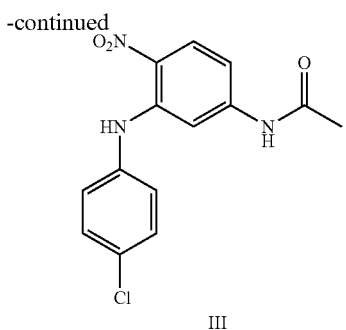

III

Procedure A: Preparation of N-(3-((4-chlorophenyl)amino)-4-nitrophenyl)acetamide III A mixture of N-(3-fluoro-4-nitrophenyl)acetamide II (10 mmol), 4-chloroaniline I (11 mmol), potassium carbonate (11 mmol) and copper iodide (1 mmol) in 25 mL dimethylformamide was heated at reflux for 8 h. After cooling to room temperature, the reaction mixture was diluted with 50 mL water and extracted with dichoromethane. The combined organic layers were dried with MgSO$_4$, then filtered and the solvent was removed under reduced pressure. The product was purified by flash chromatography to afford the derivative III. Elemental Analysis: Calculated C, 55.00; H, 3.96; N, 13.75; Found C, 55.04; H, 3.91; N, 13.79.

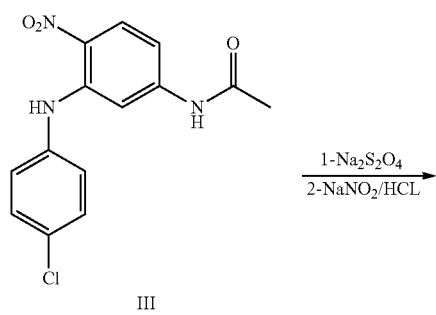

Procedure B: Preparation of N-(1-(4-chlorophenyl)-1H-benzo[d][1,2,3]triazol-6-yl)acetamide IV To a suspension of nitro derivative III (10 mmol) in ethanol (30 ml) and water (10 ml), was added Na$_2$S$_2$O$_4$ (40 mmol) and heated at reflux for 5 h. After cooling to room temperature, concentrated hydrochloric acid (15 ml) was added carefully to the reaction mixture, and heated at reflux for 30 min. The precipitate formed was filtered off and washed with a small amount of hot water. The filtrate was evaporated to about 30 ml, brought to pH=10 by adding ammonium hydroxide, and extracted with CH$_2$Cl$_2$. The combined organic layers were dried over MgSO$_4$, then filtered and the solvent was removed under reduced pressure. To the mixture of crude product in 15 mL of water and 15 mL of concentrated hydrochloric acid was added a solution of sodium nitrite (12 mmol) in 5 mL of water dropwise while maintaining the temperature of the reaction mixture at 0-5° C. The obtained mixture was stirred for an additional 1 h at 20-25°, neutralized by adding ammonium hydroxide, and filtered. The precipitate obtained was washed with ice water dried and recrystallized to yield the benzotriazol IV. Elemental Analysis: Calculated C, 58.65; H, 3.87; N, 19.54; Found C, 58.61; H, 3.92; N, 19.47.

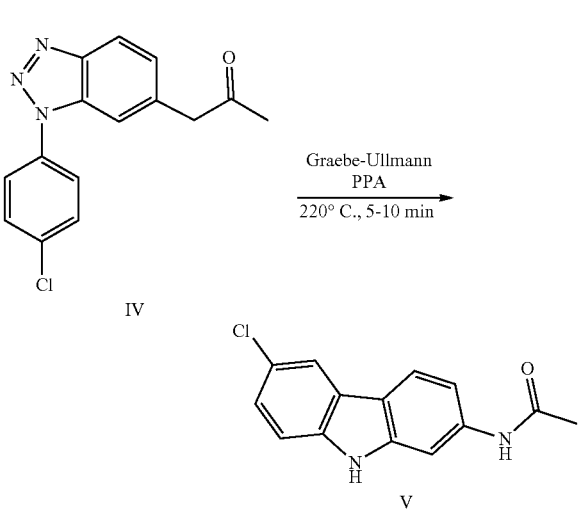

Procedure C: N-(6-chloro-9H-carbazol-2-yl)acetamide V

A suspension of benzotriazol IV (8 mmol) in PPA (2 g) was stirred and heated to 220° C. for 5 to 10 min. After cooling, the reaction mixture was dissolved in a small volume of water, made basic by adding ammonium hydroxide, and cooled. The precipitate formed was filtered off, washed with water and recrystallized to afford N-(6-chloro-9H-carbazol-2-yl)acetamide V. Elemental Analysis: Calculated C, 65.00; H, 4.29; N, 10.83; Found C, 65.06; H, 4.34; N, 10.79.

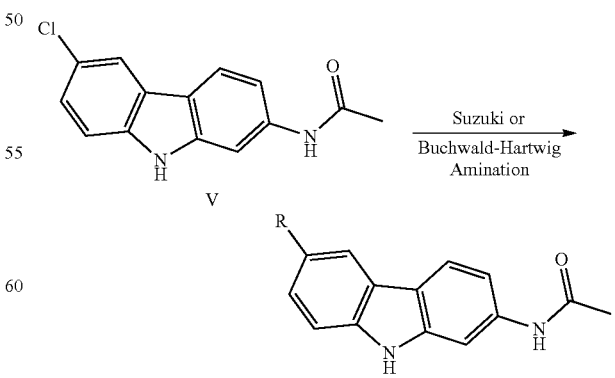

Procedure D: General Preparation of N-(6-aryl-9H-carbazol-2-yl)acetamide VIa, N-(6-arylamino-9H-carbazol-2-yl)acetamide VIb General Preparation of
N-(6-aryl-9H-carbazol-2-yl)acetamide VIa To a suspension of carbazole V (1 mmol) in toluene (10 mL) were added $Pd_2(dba)_3$ (0.1 mmol), Xantphos (0.2 mmol) and $Na_2CO_3$ (3 mmol, 2 mL $H_2O$) and arylboronic acid (1.5 mmol) and heated at reflux for 4 h under argon atmosphere, and then concentrated under reduced pressure. The crude product was dissolved in ethyl acetate (20 mL), and washed with brine and water. The combined organic layers were dried over $MgSO_4$, then filtered and the solvent was removed under reduced pressure. The product was purified by flash chromatography or by crystallization to afford the expected product VIa.

General Preparation of
N-(6-arylamino-9H-carbazol-2-yl)acetamide VIb

A sealed pressure tube with stir bar was charged with carbazole V (0.5 mmol), $[Pd_2(dba)_3]$ (37 mg, 0.04 mmol), X-Phos (38 mg, 0.08 mmol), and $K_2CO_3$ (190 mg, 1.37 mmol). The tube was evacuated and back-filled with argon (repeated for three additional times). Degassed tBuOH (1 mL) and the selected arylamine (0.65 mmol) were added and the reaction mixture was stirred at 100° C. for 12 h. After cooling to room temperature, the solution was quenched with $H_2O$ and extracted with ethyl acetate. The combined organic layers were dried over $MgSO_4$, then filtered and the solvent was removed under reduced pressure. The product was purified by flash chromatography or by crystallization to afford the expected product VIb.

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for an acute or chronic airway disease or disorder. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of a bacterial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of diseases or infections, especially bacterial infections and/or tuberculosis.

In this regard, the present subject matter relates to a method of treating a bacterial infection in a patient, comprising administering to a patient in need thereof a therapeutically effective amount of a compound as described herein.

In a further embodiment, the bacterial infection treatable herein can be caused by Gram-positive *Staphylococcus aureus, Staphylococcus aureus* resistant to MRSA, *epidermidis, Bacillus subtilis, Enterococcus faecium, Enterococcus faecium* resistant to VRE, or Gram-negative organisms including *Klebsiella pneumonia, Escherichia coli*, or *Pseudomonas aeruginosa*, or any combination thereof.

In one specific embodiment, the bacterial infection can be caused by H37Rv type of *M. tuberculosis* strains. In another specific embodiment, the bacterial infection can be caused by *E. coli*.

The compounds as described herein are not only new but have very valuable antimicrobial properties. These compounds showed a broad spectrum of activity against gram positive and gram-negative bacteria, as well tuberculosis mycobacteria. They also showed potent activity against drug resistant bacteria such as MRSA and VRSA. The molecular target of these derivatives was identified as DNA Gyrase B. Another potentially useful target herein is topoisomerase IV. Based on their pharmacological profiles, the present compounds may find important clinical applications for severe infectious diseases and tuberculosis The present subject matter also relates to the use of a compound as described herein in the manufacture of a pharmaceutical composition for the treatment of bacterial infections, such as the diseases or disorders exemplified above. In particular, the present subject matter relates to the use of a compound as described herein in the manufacture of a pharmaceutical composition for the treatment or prophylaxis of bacterial infection, such as, but not limited to, bacterial infections caused by Gram-positive *Staphylococ-* cus aureus, *Staphylococcus aureus* resistant to MRSA, *epidermidis*, *Bacillus subtilis*, *Enterococcus faecium*, *Enterococcus faecium* resistant to VRE, Gram-negative organisms including *Klebsiella pneumonia*, *Escherichia coli*, or *Pseudomonas aeruginosa*, H137Rv type of *M. tuberculosis* strains, *E. coli*, or any combination thereof.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In an embodiment, the present subject matter relates to a method of treating a bacterial infection caused by, for example, but not limited to, Gram-positive *Staphylococcus aureus*, *Staphylococcus aureus* resistant to MRSA, *epidermidis*, *Bacillus subtilis*, *Enterococcus faecium*, *Enterococcus faecium* resistant to VRE, Gram-negative organisms including *Klebsiella pneumonia*, *Escherichia coli*, or *Pseudomonas aeruginosa*, H37Rv type of *M. tuberculosis* strains, *E. coli*, or any combination thereof comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used.

The following examples relate to various methods of manufacturing certain specific compounds as described herein.

Example 1

3-(7-acetamido-9H-carbazol-3-yl)benzoic acid (1)

Compound (1) was obtained in accordance with the general preparation of N-(6-aryl-9H-carbazol-2-yl)acetamide VIa using 3-carboxyphenylboronic acid. Elemental Analysis: Calculated C, 73.24; H, 4.68; N, 8.13; Found C, 73.19; H, 4.71; N, 8.16.

Example 2

N-(6-(3-(trifluoromethoxy)phenyl)-9H-carbazol-2-yl)acetamide (2)

Compound (2) was obtained in accordance with the general preparation of N-(6-aryl-9H-carbazol-2-yl)acetamide VIa using 3-trifluoromethoxyphenylboronic acid. Elemental Analysis: Calculated C, 65.62; H, 3.93; N, 7.29; Found C, 65.68; H, 4.01; N, 7.18.

Example 3

N-(6-(3-methoxyphenyl)-9H-carbazol-2-yl)acetamide (3)

Compound (3) was obtained in accordance with the general preparation of N-(6-aryl-9H-carbazol-2-yl)acetamide VIa using 3-methoxyphenylboronic acid. Elemental Analysis: Calculated C, 76.34; H, 5.49; N, 8.48; Found C, 76.26; H, 5.55; N, 8.53.

Example 4

N-(6-(3-(trifluoromethyl)phenyl)-9H-carbazol-2-yl)acetamide (4)

Compound (4) was obtained in accordance with the general preparation of N-(6-aryl-9H-carbazol-2-yl)acetamide VIa using 3-trifluoromethylphenylboronic acid. Elemental Analysis: Calculated C, 68.47; H, 4.10; N, 7.61; Found C, 68.54; H, 4.08; N, 7.53.

Example 5

N-(6-(2-methoxypyrimidin-5-yl)-9H-carbazol-2-yl)acetamide (5)

Compound (5) was obtained in accordance with the general preparation of N-(6-aryl-9H-carbazol-2-yl)acetamide VIa using 2-methoxypyrimidine-5-boronic acid. Elemental Analysis: Calculated C, 68.66; H, 4.85; N, 16.86; Found C, 68.71; H, 4.88; N, 16.93.

Example 6

3-((7-acetamido-9H-carbazol-3-yl)amino)benzoic acid (6)

Compound (6) was obtained in accordance with the general preparation of N-(6-aryl-9H-carbazol-2-yl)acetamide VIb using 3-aminobenzoic acid. Elemental Analysis: Calculated C, 70.18; H, 4.77; N, 11.69; Found C, 70.14; H, 4.74; N, 11.72.

Example 7

N-(6-((3-(trifluoromethoxy)phenyl)amino)-9H-carbazol-2-yl)acetamide (7)

Compound (7) was obtained in accordance with the general preparation of N-(6-aryl-9H-carbazol-2-yl)acetamide VIb using 3-trifluoromethoxyaniline. Elemental Analysis: Calculated C, 63.16; H, 4.04; N, 10.52; Found C, 63.25; H, 4.08; N, 10.44.

Example 8

N-(6-((3-methoxyphenyl)amino)-9H-carbazol-2-yl)acetamide (8)

Compound (8) was obtained in accordance with the general preparation of N-(6-aryl-9H-carbazol-2-yl)acetamide VIb using 3-methoxyaniline. Elemental Analysis: Calculated C, 73.03; H, 5.54; N, 12.17; Found C, 72.97; H, 5.59; N, 12.06.

Example 9

N-(6-((3-(trifluoromethyl)phenyl)amino)-9H-carbazol-2-yl)acetamide (9)

Compound (9) was obtained in accordance with the general preparation of N-(6-aryl-9H-carbazol-2-yl)acetamide VIb using 3-trifluoromethylaniline. Elemental Analysis: Calculated C, 65.79; H, 4.21; N, 10.96; Found C, 65.71; H, 4.23; N, 11.11.

Example 10

N-(6-(pyridin-3-ylamino)-9H-carbazol-2-yl)acetamide (10)

Compound (10) was obtained in accordance with the general preparation of N-(6-aryl-9H-carbazol-2-yl)acetamide VIb using 3-aminopyridine. Elemental Analysis: Calculated C, 72.13; H, 5.10; N, 17.71; Found C, 72.20; H, 5.04; N, 17.63.

Example 11

Antibacterial Activity Evaluation

The following example relates to the antibacterial effectiveness of certain specific compounds as described herein.

Compounds 1-10 as identified above were evaluated for in vitro antibacterial activity according to the reported procedure (*Methods for Dilution Antimicrobial Susceptibility Tests for Bacteria That Grow Aerobically; Approved Standard—Tenth Edition*. CLSI document M07-A10. Wayne. PA: Clinical and Laboratory Standards Institute. 2015) against bacterial strains comprising Gram-positive *Staphylococcus aureus*, *Staphylococcus aureus* resistant to MRSA, *epidermidis*, *Bacillus subtilis*, *Enterococcus faecium*, *Enterococcus faecium* resistant to VRE, and Gram-negative organisms including *Klebsiella pneumonia*, *Escherichia coli*, *Pseudomonas aeruginosa*.

The biological results obtained demonstrated that the present compounds possess favorable antimicrobial activity. By way of non-limiting example, the compound of Example 6 displayed promising antibacterial activity against various drug sensitive and drug resistant bacterial strains, as reported in Table 1.

TABLE 1

Antibacterial Activity of Compound 6

| Microorganisms | Compound 6 | Ciprofloxacin MIC ug/mL | Vancomycin |
|---|---|---|---|
| *Staphylococcus aureus* ATCC 29213 | 1 | 0.5 | 1 |
| *Staphylococcus aureus* ATCC BAA-1556 (MERSA resistant) | 1 | 16 | 1 |
| *Staphylococcus epidermidis* | 1 | 0.25 | 1 |
| *Bacillus subtilis* MTCC 441 | 0.25 | 0.25 | 0.5 |
| *Enterococcus faecium* ATCC 35667 | 2 | 4 | 0.5 |
| *Enterococcus faecium* ATCC 51559 (VRE resistant) | 1 | 16 | >128 |
| *Klebsiella pneumonia* MTCC 618 | 0.75 | 0.75 | >128 |
| *Escherichia coli* MTCC 443 | 0.5 | 0.05 | >128 |
| *Pseudomonas aeruginosa* MTCC 741 | 0.5 | 0.75 | >128 |

Example 12

Anti-Tubercular Properties

The antitubercular property of the compounds 1-10 was evaluated towards H37Rv type of *M. tuberculosis* strains. The inoculum was prepared from fresh Lowenstein-Jensen re-suspended in 7H9-5 medium (7H9 broth, 0.5% glycerol, 0.1% casitone, supplemented with oleic acid/albumin/dextrose/catalase (OADC), adjusted to a McFarland tube No. 1 and further diluted using sterile saline 1:20; 100 µL was used as inoculums. Each drug stock solution was thawed and diluted in 7H9-S at fourfold the final highest concentration assessed. Using one hundred microliter volume of 7H9-S broth, serial two-fold dilution was prepared of each drug directly in a sterile 96-well micro-titer plate. On each microplate, a growth control that did not contain any antibiotic and composed of a sterile control were also effectuated. As water and media commonly evaporate from the closest wells to the plate perimeter during culture, sterile water was added to the perimeters of the wells to prevent evaporation during the incubation. The plate was covered then sealed in plastic bag and incubated at a temperature of 37° C. in normal atmosphere. After seven days of incubation, alamar blue solution (30 mL) was added to each well and the plate was re-incubated overnight. 50 µL of alamar blue having 0.25 µM concentration were added. A change in color from blue (oxidized state) to pink (reduced) indicated the growth of bacteria and MIC was defined as the lowest concentration of drug that prevented this change in color.

The biological results demonstrated that the present compounds possess favorable anti-mycobacterial activity. By way of example, the compound of Example 6 displayed a promising anti-mycobacterial activity of 1 µg/mL against *Mycobacterium tuberculosis* H37Rv strain.

Example 13

Evaluation of Inhibitory Activities on *E. coli* DNA Gyrase

Inhibitory potencies were investigated utilizing the Inspiralis assay on streptavidin-coated 96-well microtiter plates. First, the plates were rehydrated with buffer (20 mM Tris-HCl with pH 7.6, 0.01% w/v BSA, 0.05% v/v Tween 20, 137 mM NaCl) and the biotinylated oligonucleotide was then immobilized. After washing off the unbound oligonucleotide, the enzyme test was performed. The reaction volume of 30 µL in buffer (35 mM Tris×HCl with pH 7.5, 4 mM MgCl2, 24 mM KCl, 2 mM DTT, 1.8 mM spermidine, 1 mM ATP, 6.5% w/v glycerol, 0.1 mg/mL albumin) contained 1.5 U of DNA gyrase from *E. coli*, 0.75 µg of relaxed pNO1 plasmid, and 3 µL solution of the inhibitor in 10% DMSO and 0.008% Tween 20. Reaction solutions were incubated at 37° C. for 30 min. After that, the TF buffer (50 mM NaOAc with pH 5.0, 50 mM NaCl and 50 mM MgCl2) was added to terminate the enzymatic reaction. After additional incubation for 30 min at rt, during which biotinoligonucleotide-plasmid triplex was formed, the unbound plasmid was washed off using TF buffer and SybrGOLD in T10 buffer (10 mM Tris HCl with pH 8.0 and 1 mM EDTA) was added. The fluorescence was measured with a microplate reader (BioTek Synergy H4, excitation: 485 nm, emission: 535 nm). Initial screening was done at 100 or 10 µM concentration of inhibitors. For the most active inhibitors, IC50 was determined using seven concentrations of the tested compounds. GraphPad Prism software was used to calculate the IC50 values. The result is given as the average value of three independent measurements. Novobiocin was used as a positive control.

The biological results demonstrated that the present compounds possessed favorable DNA Gyrase activity. By way of example, the compound of Example 6 displayed promising *E. coli* DNA Gyrase of 125 nM. In the same experimental condition, the reference control Novabiocin inhibited *E. coli* DNA Gyrase activity of 150 nM.

It is to be understood that the carbazole compounds as antibacterial agents are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

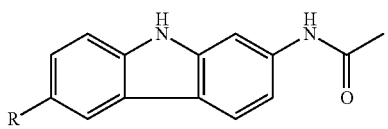

I or a pharmaceutically acceptable salt, ester, stereoisomer, or solvate thereof, wherein:
R is an aryl, heteroaryl, arylamine, or heteroarylamine, each of which may be optionally substituted with from one to three substituents independently selected from the group consisting of hydrogen, a carboxylic acid group, a trihalolkoxy group, a trihaloalkyl group, and an alkoxy group.

2. The compound as recited in claim 1, wherein each substituent of the from one to three substituents for R is independently selected from the group consisting of hydrogen, a carboxylic acid group, a trifluoromethoxy group, a trifluoromethyl group, and a methoxy group.

3. The compound as recited in claim 1, wherein R is a phenyl, a pyrimidine, or a pyridine, each of which may be optionally substituted with from one to three substituents.

4. The compound as recited in claim 1, wherein R is an amino phenyl, an amino pyrimidine, or an amino pyridine.

5. The compound as recited in claim 1, wherein R is a phenyl, a pyrimidine, a pyridine, an amino phenyl, an amino pyrimidine, or an amino pyridine, each of which phenyl, pyrimidine, and pyridine may be optionally substituted with from one to three substituents independently selected from the group consisting of hydrogen, a carboxylic acid group, a trifluoromethoxy group, a trifluoromethyl group, and a methoxy group.

6. The compound as recited in claim 1, wherein the compound is selected from the group consisting of:
3-(7-acetamido-9H-carbazol-3-yl)benzoic acid (1);
N-(6-(3-(trifluoromethoxy)phenyl)-9H-carbazol-2-yl)acetamide (2);
N-(6-(3-methoxyphenyl)-9H-carbazol-2-yl)acetamide (3);
N-(6-(3-(trifluoromethyl)phenyl)-9H-carbazol-2-yl)acetamide (4);
N-(6-(2-methoxypyrimidin-5-yl)-9H-carbazol-2-yl)acetamide (5);
3-((7-acetamido-9H-carbazol-3-yl)amino)benzoic acid (6);
N-(6-((3-(trifluoromethoxy)phenyl)amino)-9H-carbazol-2-yl)acetamide (7);
N-(6-((3-methoxyphenyl)amino)-9H-carbazol-2-yl)acetamide (8);
N-(6-((3-(trifluoromethyl)phenyl)amino)-9H-carbazol-2-yl)acetamide (9);
N-(6-(pyridin-3-ylamino)-9H-carbazol-2-yl)acetamide (10);

and a pharmaceutically acceptable salt, ester, stereoisomer, or solvate thereof.

7. A pharmaceutical composition comprising a therapeutically effective amount of the compound of claim 1 and a pharmaceutically acceptable carrier.

8. A method of treating a bacterial infection in a patient, comprising administering to a patient in need thereof a therapeutically effective amount of the compound of claim 1.

9. The method of claim 8, wherein the bacterial infection is caused by Gram-positive *Staphylococcus aureus*, *Staphylococcus aureus* resistant to MRSA, *epidermidis*, *Bacillus subtilis*, *Enterococcus faecium*, *Enterococcus faecium* resistant to VRE, or Gram-negative organisms including *Klebsiella pneumonia*, *Escherichia coli*, or *Pseudomonas aeruginosa*.

10. The method of claim 8, wherein the bacterial infection is caused by H37Rv type of *M. tuberculosis* strains.

11. The method of claim 9, wherein the bacterial infection is caused by *E. coli*.

12. A compound having the formula I:

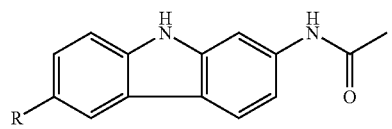

I or a pharmaceutically acceptable salt, ester, stereoisomer, or solvate thereof, wherein
R is a phenyl, a pyrimidine, a pyridine, an amino phenyl, an amino pyrimidine, or an amino pyridine, each of which phenyl, pyrimidine, and pyridine may be optionally substituted with from one to three substituents independently selected from the group consisting of hydrogen, a carboxylic acid group, a trifluoromethoxy group, a trifluoromethyl group, and a methoxy group.

13. A pharmaceutical composition comprising a therapeutically effective amount of the compound of claim 12 and a pharmaceutically acceptable carrier.

14. A method of treating a bacterial infection in a patient, comprising administering to a patient in need thereof a therapeutically effective amount of the compound of claim 12.

15. A compound selected from the group consisting of:
3-(7-acetamido-9H-carbazol-3-yl)benzoic acid (1);
N-(6-(3-(trifluoromethoxy)phenyl)-9H-carbazol-2-yl)acetamide (2);
N-(6-(3-methoxyphenyl)-9H-carbazol-2-yl)acetamide (3);
N-(6-(3-(trifluoromethyl)phenyl)-9H-carbazol-2-yl)acetamide (4);
N-(6-(2-methoxypyrimidin-5-yl)-9H-carbazol-2-yl)acetamide (5);
3-((7-acetamido-9H-carbazol-3-yl)amino)benzoic acid (6);
N-(6-((3-(trifluoromethoxy)phenyl)amino)-9H-carbazol-2-yl)acetamide (7);
N-(6-((3-methoxyphenyl)amino)-9H-carbazol-2-yl)acetamide (8);
N-(6-((3-(trifluoromethyl)phenyl)amino)-9H-carbazol-2-yl)acetamide (9);

N-(6-(pyridin-3-ylamino)-9H-carbazol-2-yl)acetamide (10);

and a pharmaceutically acceptable salt, ester, stereoisomer, or solvate thereof.

16. A pharmaceutical composition comprising a therapeutically effective amount of the compound of claim 15 and a pharmaceutically acceptable carrier.

17. A method of treating a bacterial infection in a patient, comprising administering to a patient in need thereof a therapeutically effective amount of the compound of claim 15.

\* \* \* \* \*